US00PP19510P2

(12) United States Plant Patent
Zary

(10) Patent No.: US PP19,510 P2
(45) Date of Patent: Dec. 2, 2008

(54) FLORIBUNDA ROSE PLANT NAMED 'JACREPIN'

(50) Latin Name: *Rosa hybrida*
Varietal Denomination: JACrepin

(75) Inventor: Keith W. Zary, Thousand Oaks, CA (US)

(73) Assignee: Jackson & Perkins Wholesale, Inc., Hodges, SC (US)

( * ) Notice: Subject to any disclaimer, the term of this patent is extended or adjusted under 35 U.S.C. 154(b) by 0 days.

(21) Appl. No.: 11/998,254

(22) Filed: Nov. 28, 2007

(51) Int. Cl.
*A01H 5/00* (2006.01)

(52) U.S. Cl. ..... Plt./151

(58) Field of Classification Search ..... Plt./151
See application file for complete search history.

*Primary Examiner*—Kent L. Bell
*Assistant Examiner*—Georgia Helmer
(74) *Attorney, Agent, or Firm*—Klarquist Sparkman LLP

(57) ABSTRACT

Floribunda rose plant having very glossy, dark green foliage, ease of own root propagation; vigorous growth on its own roots; rounded, well branched habit of growth; and flowers presented in clusters.

1 Drawing Sheet

Genus and species: *Rosa hybrida.*
Variety Denomination: 'JACrepin'.

ORIGIN OF THE INVENTION

The present invention relates to a new and distinct variety of a floribunda rose plant named 'JACrepin', which was originated by me by crossing the variety 'JACimpac' (not patented, seed parent), with the variety 'JACtorse' (U.S. Plant Pat. No. 12,129, pollen parent). The parentage of the seed parent is 'JACdew' (U.S. Plant Pat. No. 5,122)× 'HARrooney' (U.S. Plant Pat. No. 5,582).

BACKGROUND OF THE INVENTION

The primary objective of this breeding was to produce a new floribunda rose variety having the rounded plant habit, flower clusters and glossy foliage of the coral colored floribunda female (seed) parent combined with the vigorous growth, own root ease of propagation and growth and good flower form of the male (pollen) parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Very glossy, dark green foliage.
2. Ease of own root propagation.
3. Vigorous growth on its own roots.
4. Rounded, well branched habit of growth.
5. Flowers presented in clusters.

Asexual reproduction of this new variety by cuttings, as performed at Wasco, Calif., shows that the foregoing characteristics and distinctions come true to form and are established and transmitted through succeeding propagations.

COMPARISON WITH PARENTS

'JACrepin' differs in flower color from the flower color of the female parent (coral) and the flower color of the male parent (deep pink with light yellow petal reverse).

COMPARISON WITH SIMILAR VARIETY

The closest variety known to the inventor is 'JACzibwo' (U.S. Plant Pat. No. 14,245). 'JACrepin' differs from 'JACzibwo' in flower form (high centered from 'JACrepin' versus quite flat for 'JACzibwo') and in petal count ('JACrepin' typically having 20 to 25 petals versus typically 15 to 20 petals for 'JACzibwo'.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart® 2001, except where ordinary dictionary significance of color is indicated.

Parentage:

*Seed parent.*—'JACimpac' (not patented). Parentage of seed parent is 'JACdew' (U.S. Plant Pat. No. 5,122)× 'HARrooney' (U.S. Plant Pat. No. 5,582).

*Pollen parent.*—'JACtorse' (U.S. Plant Pat. No. 12,129).

FLOWER

Observations made from January 2005 to October 2007 from plants that were three years of age at the end of the observation period and that were growing in a garden environment at Somis, Calif.

Blooming habit: Continuous.

Bud:

*Size.*—About 40 mm long and 30 mm in diameter when the petals start to unfurl.

*Form.*—The bud form is long, pointed ovoid.

*Color.*—When sepals first divide, bud color is Red Group 46B. When half blown, the upper sides of the petals are Red Group 46B and the lower sides of the petals are Red Group 46B.

*Sepals.*—Color: Upper surface: Green Group 138B. Lower surface: Yellow-Green Group 146B. Length: 30 mm. Width: 9 mm. Shape: Subulate. Surface: Hoary. There are three normally to heavily appendaged sepals. There are two unappendaged sepals with hairy edges.

*Receptacle.*—Color: Yellow-Green Group 146D, but can be overlain with Greyed-Purple Group 183C in bright sunlight. Shape: Funnel. Size: About 8 mm long×8–10 mm. Surface: Smooth.

*Peduncle.*—Length: Medium, averaging about 45 mm. Surface: Rough, prickly. Color: Yellow-Green Group 146C. Strength: Stiff, erect.

Bloom:

*Size.*—Large. Average open diameter is about 90–95 mm.

*Borne.*—Singly and several together in clusters of 3–5 blooms having a pyramidal shape.

*Stems.*—Strength: Strong. Average length is about 30–40 mm with a diameter of 7–8 mm.

*Form.*—When first open: High centered. Permanence: With age flattens, all petals curl.

*Petalage.*—Number of petals under normal conditions: 20–25.

*Color.*—The upper sides of the petals are Red Group 46B. The reverse sides of the petals are Red Group 46D. The base of the petals has a Yellow Group 6C color spot, about 8 mm×8 mm in size. The major color on the upper sides is Red Group 46B.

*Variegations.*—Occasional white streaks (White Group 155C) on guard petals.

*Discoloration.*—The general tonality at the end of the first day. No change. At the end of the third day: Fading to Red Group 46C. By day 5, Red Group 46D.

*Fragrance.*—Slight, peppery.

Petals:

*Thickness.*—Thick.

*Surface texture.*—Smooth.

*Shape.*—Oval to deltoid.

*Margin.*—Entire.

*Apex shape.*—Rounded.

*Base shape.*—Rounded to cuneate.

*Form.*—Tips slightly recurved.

*Arrangement.*—Imbricated.

*Petaloids.*—Number: Few, 0 to 3.

*Persistence.*—Petals drop off cleanly before drying.

*Lastingness.*—On the plant: Fair (about 5–6 days). As a cut flower: Fair (about 6–7 days).

Reproductive parts:

*Stamens.*—Number: 70–80. Length: 8–9 mm. Anthers: Length: 3 mm. Color: Yellow-Orange Group 22B. Arrangement: Regular around styles. Filaments: Color: Red Group 46D. Length: 5–6 mm. Pollen: Color: Orange Group 26B.

*Pistils.*—Number: 40–45. Length: 4 mm. Styles: Color: Red Group 53B on the upper 1 mm and Yellow-White Group 158D over the rest. Length: 3 mm. Stigmas: Color: White Group 155D. Length: 1 mm. Hips: None observed.

PLANT

*Form.*—Bush.

*Growth.*—Vigorous, upright, branching.

*Age to maturity.*—Two years.

*Mature plant.*—Height: 80–90 cm. Width: 65–75 cm.

*Rootstock.*—Own roots.

Foliage: Number of leaflets on normal mid-stem leaves: 5 or 7.

*Size.*—Large. About 150 mm long×110 mm wide.

*Quantity.*—Abundant.

*Color.*—New foliage: Upper side: Greyed-Purple Group 183A. Lower side: Greyed-Purple Group 183A. Old foliage: Upper side: Green Group 139A. Lower side: Yellow-Green Group 146B.

Leaflets:

*Size.*—About 50 mm long×40 mm wide.

*Shape.*—Ovate.

*Base shape.*—Rounded.

*Apex shape.*—Acuminate.

*Texture.*—Leathery, glossy.

*Edge.*—Serrated.

*Serrations.*—Single.

*Petiole.*—Color: Yellow-Green Group 146D.

*Petiole rachis.*—Color: Yellow-Green Group 146D. Underside: Rough wide prickles.

*Stipules.*—Length: 15–17 mm, smooth, edge in glands.

*Disease resistance.*—Resistant to rust, susceptible to blackspot and mildew under normal growing conditions.

*Pest resistance.*—None observed.

*Vein color.*—Yellow-Green Group 146D.

*Venation pattern.*—Reticulate.

Wood:

*New wood.*—Color: Yellow-Green Group 146B, but early on overlaid with Greyed-Purple Group 183A. Bark: Smooth.

*Old wood.*—Color: Yellow-Green Group 146A. Bark: Smooth.

Prickles:

*Quantity.*—Ordinary, on main canes from base: 15–18 per 15 cm. Ordinary, on laterals from main canes: 15–18 per 15 cm.

*Form.*—Hooked upward.

*Length.*—5–7 mm.

*Color when young.*—Greyed-Purple Group 186C.

*Color when mature.*—Greyed-Orange Group 174A.

Small prickles:

*Quantity.*—On main stalks: Few, 3 or 4 per 15 cm. On laterals: Few, 3 or 4 per 15 cm.

*Color when young.*—Greyed-Purple Group 186C.

*Color when mature.*—Greyed-Orange Group 174A.

Winter hardiness: Hardy to Zone 5.

I claim:

1. A new and distinct variety of floribunda rose plant, substantially as herein shown and described, characterized particularly by very glossy, dark green foliage; ease of own root propagation; vigorous growth on its own roots; rounded, well branched habit of growth; and flowers presented in clusters.

* * * * *

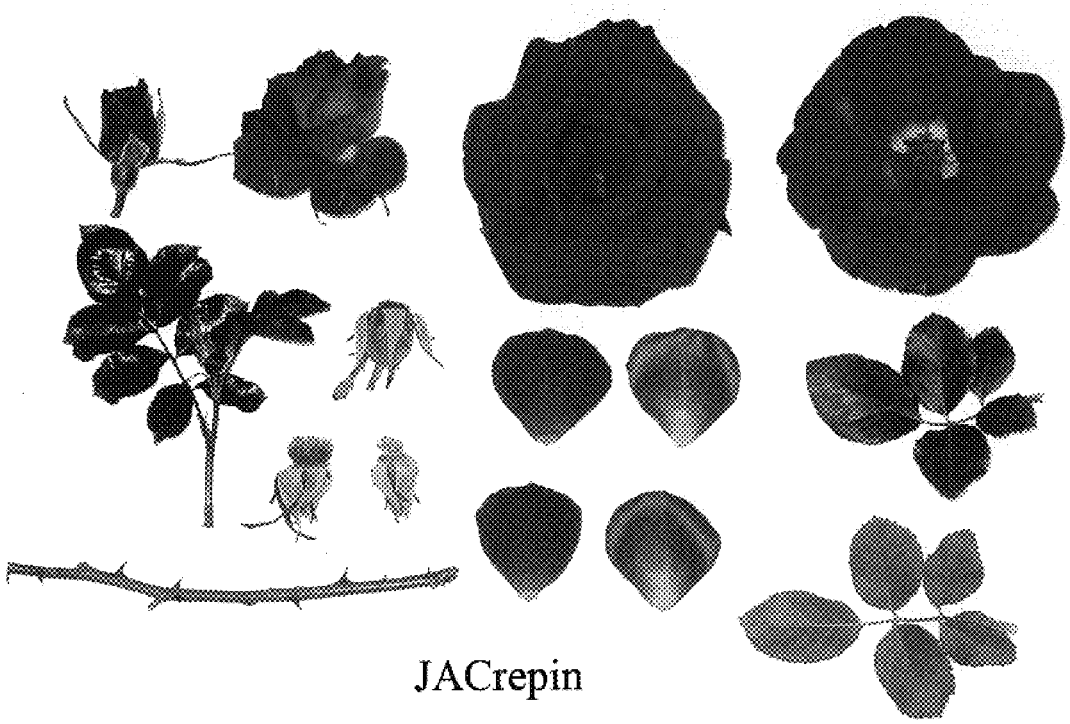
JACrepin

UNITED STATES PATENT AND TRADEMARK OFFICE

CERTIFICATE OF CORRECTION

PATENT NO. : PP 19,510 P2
APPLICATION NO. : 11/998254
DATED : December 2, 2008
INVENTOR(S) : Keith W. Zary It is certified that error appears in the above-identified patent and that said Letters Patent is hereby corrected as shown below:

In the Specification:

Column 2, line 10, "high centered from" should read --high centered for--

Column 2, line 28, "Colour Chart® 2001" should read --Colour Chart© 2001--

Column 3, line 45, "first day. No change." should read --first day: No change.--

Column 4, line 32, "Rough wide prickles." should read --Rough with prickles.--

Column 4, line 33, "edge in" should read --edged in--

Signed and Sealed this

Tenth Day of August, 2010

David J. Kappos

David J. Kappos
*Director of the United States Patent and Trademark Office*